United States Patent
Jiang et al.

(10) Patent No.: US 11,021,690 B2
(45) Date of Patent: Jun. 1, 2021

(54) MUTANT-TYPE URICASE, PEG MODIFIED MUTANT-TYPE URICASE, AND APPLICATION THEREOF

(71) Applicant: SHANGHAI INSTITUTE OF BIOLOGICAL PRODUCTS CO., LTD., Shanghai (CN)

(72) Inventors: Yun Jiang, Shanghai (CN); Linqiu Huang, Shanghai (CN); Jueren Lou, Shanghai (CN)

(73) Assignee: SHANGHAI INSTITUTE OF BIOLOGICAL PRODUCTS CO., LTD., Shanghai (CN)

( * ) Notice: Subject to any disclaimer, the term of this patent is extended or adjusted under 35 U.S.C. 154(b) by 42 days.

(21) Appl. No.: 15/764,495

(22) PCT Filed: Aug. 19, 2016

(86) PCT No.: PCT/CN2016/096094
§ 371 (c)(1),
(2) Date: Mar. 29, 2018

(87) PCT Pub. No.: WO2017/054590
PCT Pub. Date: Apr. 6, 2017

(65) Prior Publication Data
US 2018/0282707 A1     Oct. 4, 2018

(30) Foreign Application Priority Data

Sep. 29, 2015  (CN) .......................... 201510638339.9

(51) Int. Cl.
C12N 9/06       (2006.01)
A61K 47/60      (2017.01)
C12Q 1/62       (2006.01)
A61K 38/00      (2006.01)

(52) U.S. Cl.
CPC ............ *C12N 9/0048* (2013.01); *A61K 47/60* (2017.08); *C12Q 1/62* (2013.01); *C12Y 107/03003* (2013.01); *A61K 38/00* (2013.01)

(58) Field of Classification Search
None
See application file for complete search history.

(56) References Cited

U.S. PATENT DOCUMENTS 8,586,535 B2 *  11/2013  Fan ...................... C12N 9/0048
                                                          435/191
2019/0048327 A1 *  2/2019  Baca ............. C12Y 107/03003

FOREIGN PATENT DOCUMENTS

| CN | 101280293 | 8/2008 |
| CN | 101265467 | 9/2008 |
| CN | 101327327 | 12/2008 |
| WO | 2006110761 | 10/2006 |

OTHER PUBLICATIONS

Tian et al.,"PEGylation enhancement of pH stability of uricase via inhibitive tetramer dissociation", Journal of Pharmacy and Pharmacology 65: 53-63 (2012) (Year: 2012).*
Bayol et al.,"Modification of a reactive cysteine explains differences between rasburicase and Uricozyme, a natural Aspergillus favus uricase", Biotechnol. Appl. Biochem. 36: 21-31 (Year: 2002).*
Gentle et al.,"Direct Production of Proteins with N-terninal Cysteine for Site-Specific Conjugation", Bioconjugate Chem. 15: 658-663 (Year: 2004).*
Roberts et al.,"Chemistry for peptide and protein PEGylation", Advanced Drug Delivery Reviews 54: 459-476 (Year: 2002).*
Zalipsky, S.,"Functionalized Polyethylene glycol) for preparation of biologically relevant conjugates", Bioconjugate Chem. 6: 150-165 (Year: 1995).*
Dong et al., "Site-Specific PEGylation Strategies for Proteins and Peptides" Pharmaceutical and Clinical Research, vol. 21, No. 4, Aug. 31, 2013 (Aug. 31, 2013).
Wu et al., "PEG Modification of Protein Drug" Progress in Pharmaceutical Sciences, vol. 26, No. 3, Jun. 30, 2002 (Jun. 30, 2002) pp. 146-151.
Sherman et al., "PEG-uricase in the management of treatment-resistant gout and hyperuricemia," Advanced Drug Delivery Reviews, vol. 60, Aug. 14, 2007 (Aug. 14, 2007) pp. 59-68.
PCT/CN2016/096094 International Search Report and Written Opinion of the International Searching Authority dated Nov. 9, 2016 (12 pages).

* cited by examiner

*Primary Examiner* — Anand U Desai
(74) *Attorney, Agent, or Firm* — Michael Best & Friedrich LLP

(57) ABSTRACT

A mutant-type uricase, PEG modified mutant-type uricase, and application thereof. The mutant-type uricase has a cysteine residue introduced by recombination, the cysteine residue is located at an inactive region of the uricase, and one or more PEGs are coupled to the mutant-type uricase. The resulting PEGylated mutant-type uricase has characteristics of a half-life extension, product uniformity, and stable enzyme activity. Therefore, the present invention has a wide future application range.

9 Claims, 7 Drawing Sheets

Specification includes a Sequence Listing.

SEQUENCE LISTING

<160> NUMBER OF SEQ ID NOS: 15

<210> SEQ ID NO 1
<211> LENGTH: 304
<212> TYPE: PRT
<213> ORGANISM: artificial sequence
<220> FEATURE:
<223> OTHER INFORMATION: wild-type uricase

<400> SEQUENCE: 1

```
Met Ala His Tyr Arg Asn Asp Tyr Lys Lys Asn Asp Glu Val Glu Phe
1               5                   10                  15

Val Arg Thr Gly Tyr Gly Lys Asp Met Ile Lys Val Leu His Ile Gln
            20                  25                  30

Arg Asp Gly Lys Tyr His Ser Ile Lys Glu Val Ala Thr Ser Val Gln
        35                  40                  45

Leu Thr Leu Ser Ser Lys Lys Asp Tyr Leu His Gly Asp Asn Ser Asp
    50                  55                  60

Val Ile Pro Thr Asp Thr Ile Lys Asn Thr Val Asn Val Leu Ala Lys
65                  70                  75                  80

Phe Lys Gly Ile Lys Ser Ile Glu Thr Phe Ala Val Thr Ile Cys Glu
                85                  90                  95

His Phe Leu Ser Ser Phe Lys His Val Ile Arg Ala Gln Val Tyr Val
            100                 105                 110

Glu Glu Val Pro Trp Lys Arg Phe Glu Lys Asn Gly Val Lys His Val
        115                 120                 125

His Ala Phe Ile Tyr Thr Pro Thr Gly Thr His Phe Cys Glu Val Glu
    130                 135                 140
```

-continued

```
Gln Ile Arg Asn Gly Pro Pro Val Ile His Ser Gly Ile Lys Asp Leu
145                 150                 155                 160

Lys Val Leu Lys Thr Thr Gln Ser Gly Phe Glu Gly Phe Ile Lys Asp
                165                 170                 175

Gln Phe Thr Thr Leu Pro Glu Val Lys Asp Arg Cys Phe Ala Thr Gln
            180                 185                 190

Val Tyr Cys Lys Trp Arg Tyr His Gln Gly Arg Asp Val Asp Phe Glu
        195                 200                 205

Ala Thr Trp Asp Thr Val Arg Ser Ile Val Leu Gln Lys Phe Ala Gly
    210                 215                 220

Pro Tyr Asp Lys Gly Glu Tyr Ser Pro Ser Val Gln Lys Thr Leu Tyr
225                 230                 235                 240

Asp Ile Gln Val Leu Ser Leu Gly Arg Val Pro Glu Ile Glu Asp Met
                245                 250                 255

Glu Ile Ser Leu Pro Asn Ile His Tyr Phe Asn Ile Asp Met Ser Lys
                260                 265                 270

Met Gly Leu Ile Asn Lys Glu Glu Val Leu Leu Pro Leu Asp Asn Pro
            275                 280                 285

Tyr Gly Lys Ile Thr Gly Thr Val Lys Arg Lys Leu Ser Ser Arg Leu
    290                 295                 300
```

<210> SEQ ID NO 2
<211> LENGTH: 248
<212> TYPE: PRT
<213> ORGANISM: artificial sequence
<220> FEATURE:
<223> OTHER INFORMATION: mutant uricase

<400> SEQUENCE: 2

```
Met Ala His Tyr Arg Asn Asp Tyr Lys Lys Asn Asp Glu Val Glu Phe
1               5                   10                  15

Val Arg Thr Gly Tyr Gly Lys Asp Met Ile Lys Val Leu His Ile Gln
                20                  25                  30

Arg Asp Gly Lys Tyr His Ser Ile Lys Glu Val Ala Thr Ser Val Gln
            35                  40                  45

Leu Thr Leu Ser Ser Lys Lys Asp Tyr Leu His Gly Asp Asn Ser Asp
        50                  55                  60

Val Ile Pro Thr Asp Thr Ile Lys Asn Thr Val Asn Val Leu Ala Lys
65                  70                  75                  80

Phe Lys Gly Ile Lys Ser Ile Glu Thr Phe Ala Val Thr Ile Cys Glu
                85                  90                  95

His Phe Leu Ser Ser Phe Cys His Val Ile Arg Ala Gln Val Tyr Val
            100                 105                 110

Glu Glu Val Pro Trp Lys Arg Phe Glu Lys Asn Gly Val Lys His Val
        115                 120                 125

His Ala Phe Ile Tyr Thr Pro Thr Gly Thr His Phe Cys Glu Val Glu
    130                 135                 140

Gln Ile Arg Asn Gly Pro Pro Val Ile His Ser Gly Ile Lys Asp Leu
145                 150                 155                 160

Lys Val Leu Lys Thr Thr Gln Ser Gly Phe Glu Gly Phe Ile Lys Asp
                165                 170                 175

Gln Phe Thr Thr Leu Pro Glu Val Lys Asp Arg Cys Phe Ala Thr Gln
            180                 185                 190

Val Tyr Cys Lys Trp Arg Tyr His Gln Gly Arg Asp Val Asp Phe Glu
        195                 200                 205
```

Ala Thr Trp Asp Thr Val Arg Ser Ile Val Leu Gln Lys Phe Ala Gly
    210                 215                 220

Pro Tyr Asp Lys Gly Glu Tyr Ser Pro Ser Val Gln Lys Thr Leu Tyr
225                 230                 235                 240

Asp Ile Gln Val Leu Ser Leu Gly
            245

<210> SEQ ID NO 3
<211> LENGTH: 915
<212> TYPE: DNA
<213> ORGANISM: artificial sequence
<220> FEATURE:
<223> OTHER INFORMATION: mutant uricase

<400> SEQUENCE: 3

| | | | |
|---|---|---|---|
| atggctcatt accgtaatga ctacaaaaag aatgatgagg tagagtttgt ccgaactggc | 60 |
| tatgggaagg atatgataaa agttctccat attcagcgag atggaaaata tcacagcatt | 120 |
| aaagaggtgg caacttcagt gcaactgact ttgagctcca aaaaagatta cctgcatgga | 180 |
| gacaattcag atgtcatccc tacagacacc atcaagaaca cagttaatgt cctggcgaag | 240 |
| ttcaaaggca tcaaaagcat agaaactttt gctgtgacta tctgtgagca tttcctttct | 300 |
| tccttctgtc atgtcatcag agctcaagtc tatgtggaag aagttccttg gaagcgtttt | 360 |
| gaaaagaatg gagttaagca tgtccatgca tttatttata ctcctactgg aacgcacttc | 420 |
| tgtgaggttg aacagataag gaatggacct ccagtcattc attctggaat caaagaccta | 480 |
| aaagtcttga aaacaaccca gtctggcttt gaaggattca tcaaggacca gttcaccacc | 540 |
| ctccctgagg tgaaggaccg gtgctttgcc acccaagtgt actgcaaatg cgctaccac | 600 |
| cagggcagag atgtggactt tgaggccacc tgggacactg ttaggagcat tgtcctgcag | 660 |
| aaatttgctg ggcccatga caaaggcgag tactcaccct ctgtgcagaa gaccctctat | 720 |
| gatatccagg tgctctccct gagccgagtt cctgagatag aagatatgga aatcagcctg | 780 |
| ccaaacattc actacttcaa tatagacatg tccaaaatgg gtctgatcaa caaggaagag | 840 |
| gtcttgctgc cattagacaa tccatatgga aaaattactg gtacagtcaa gaggaagttg | 900 |
| tcttcaagac tgtga | 915 |

<210> SEQ ID NO 4
<211> LENGTH: 25
<212> TYPE: DNA
<213> ORGANISM: artificial sequence
<220> FEATURE:
<223> OTHER INFORMATION: primer

<400> SEQUENCE: 4
gcatccgatg acccaatcca tggct       25

<210> SEQ ID NO 5
<211> LENGTH: 25
<212> TYPE: DNA
<213> ORGANISM: artificial sequence
<220> FEATURE:
<223> OTHER INFORMATION: primer

<400> SEQUENCE: 5
acccaatgga tcctcatcac agtct       25

-continued

```
<210> SEQ ID NO 6
<211> LENGTH: 36
<212> TYPE: DNA
<213> ORGANISM: artificial sequence
<220> FEATURE:
<223> OTHER INFORMATION: primer

<400> SEQUENCE: 6
tttcctttct tccttctgtc atgtcatcag agctca                           36

<210> SEQ ID NO 7
<211> LENGTH: 36
<212> TYPE: DNA
<213> ORGANISM: artificial sequence
<220> FEATURE:
<223> OTHER INFORMATION: primer

<400> SEQUENCE: 7
tgagctctga tgacatgaca gaaggaagaa aggaaa                           36

<210> SEQ ID NO 8
<211> LENGTH: 36
<212> TYPE: DNA
<213> ORGANISM: artificial sequence
<220> FEATURE:
<223> OTHER INFORMATION: primer

<400> SEQUENCE: 8
gaggttgaac agataaggtg tggacctcca gtcatt                           36

<210> SEQ ID NO 9
<211> LENGTH: 36
<212> TYPE: DNA
<213> ORGANISM: artificial sequence
<220> FEATURE:
<223> OTHER INFORMATION: primer

<400> SEQUENCE: 9
aatgactgga ggtccacacc ttatctgttc aacctc                           36

<210> SEQ ID NO 10
<211> LENGTH: 36
<212> TYPE: DNA
<213> ORGANISM: artificial sequence
<220> FEATURE:
<223> OTHER INFORMATION: primer

<400> SEQUENCE: 10
aaggattcat caaggactgc ttcaccaccc tccctg                           36

<210> SEQ ID NO 11
<211> LENGTH: 36
<212> TYPE: DNA
<213> ORGANISM: artificial sequence
<220> FEATURE:
<223> OTHER INFORMATION: primer

<400> SEQUENCE: 11
cagggagggt ggtgaagcag tccttgatga atcctt                           36

<210> SEQ ID NO 12
<211> LENGTH: 32
<212> TYPE: DNA
<213> ORGANISM: artificial sequence
<220> FEATURE:
<223> OTHER INFORMATION: primer
```

```
<400> SEQUENCE: 12
cgctaccacc agtgcagaga tgtggactttga                              32

<210> SEQ ID NO 13
<211> LENGTH: 32
<212> TYPE: DNA
<213> ORGANISM: artificial sequence
<220> FEATURE:
<223> OTHER INFORMATION: primer

<400> SEQUENCE: 13
tcaaagtcca catctctgca ctggtggtag cg                             32

<210> SEQ ID NO 14
<211> LENGTH: 35
<212> TYPE: DNA
<213> ORGANISM: artificial sequence
<220> FEATURE:
<223> OTHER INFORMATION: primer

<400> SEQUENCE: 14
aatttgctgg gccctatgac tgtggcgagt actca                          35

<210> SEQ ID NO 15
<211> LENGTH: 35
<212> TYPE: DNA
<213> ORGANISM: artificial sequence
<220> FEATURE:
<223> OTHER INFORMATION: primer

<400> SEQUENCE: 15
tgagtactcg ccacagtcat agggcccagc aaatt                          35
```

MUTANT-TYPE URICASE, PEG MODIFIED MUTANT-TYPE URICASE, AND APPLICATION THEREOF

CROSS-REFERENCE TO RELATED APPLICATION(S)

This application is a national stage filing under 35 U.S.C. § 371 of International Application No. PCT/CN2016/096094, filed on Aug. 19, 2016, which application claims the benefit of Chinese Patent Application No. 201510638339.9, filed on Sep. 29, 2015, the entire contents of each of which are fully incorporated herein by reference.

TECHNICAL FIELD

The present invention relates to the field of proteins, and in particular, to a mutant uricase, a PEG modified mutant uricase, and a use thereof.

BACKGROUND

Urate oxidase (EC 1.7.3.3), which is also known as uricase, specifically catalyzes the oxygenolysis of a uric acid into an allantoin. Due to mutations in the uricase-encoding gene, an active urate oxidase cannot be synthesized in the human body. With the improvement of people's living standards, excessive intake of high-protein diet can result in the elevation of blood uric acid levels and then trigger hyperuricemia, and eventually develop into gout. In recent years, the incidence of chronic hyperuricemia/gout has continued to rise. According to incomplete statistics, it has reached more than 10% of the total population. In addition, hyperuricemia is also one of the serious chemotherapy side effects faced by cancer patients. Therefore, uricase preparation is not only used for the treatment of gout, but also an indispensable adjuvant therapeutic drug for cancer chemotherapy patients, the application thereof is very extensive.

Currently widely used drugs for the treatment of gout are mostly anti-inflammatory analgesics and drugs for promoting the uric acid excretion, with a great side effect. Uricase is a natural decomposing enzyme for uric acid, by which uric acid is decomposed into allantoin and excreted from the body, the side effects of which are far lower than those of the traditional therapeutics of gout. At present, there are very few commercially available uricase drugs in the world. There are currently no commercially available uricase drugs independently developed in China.

In recent years, in order to solve shortcomings of protein drugs such as short half-life in vivo and high immunogenicity, considerable progresses are obtained in the method for modifying protein drugs with PEG, and "amino modification" is the most commonly used PEG modification method, mainly for Lys-ε-amino group and α-amino group on N-terminal in Lys. This PEG modification method is adopted for Pegloticase. However, uricase is a homotetramer, and each subunit contains up to 31 Lys, and each PEG modification can only randomly and non site-targetedly modify a part of Lys, which makes the modified product very inhomogeneous and unstable.

Compared with the amino modification, sulfhydryl groups are present in the composition of a protein in low content and the position thereof is fixed, so that targeted modifications can be performed on such sulfhydryl groups that have little effects on the activity and are in a free state.

Therefore, there is an urgent need in the art to develop a new PEG modification method—the method of "PEG sulf- hydryl modification for urease" with characteristics of stability and homogeneous products.

SUMMARY OF THE INVENTION

The object of the present invention is to provide a new PEG modification method—the method of "PEG sulfhydryl modification for urease" with characteristics of stability and homogeneous products.

In the first aspect of the present invention, a mutant uricase is provided, which has a recombinantly introduced cysteine residue, and the cysteine residue is located in an inactive region of the uricase.

In another preferred embodiment, the mutant uricase has at least 70% (70%) of the enzymatic activity of the wild-type uricase (SEQ ID NO.: 1).

In another preferred embodiment, the inactive region is a region of uricase selected from a group consisting of:
(a) positions 103±3, 148±3, 177±3, 202±3, 228±3, 291±3 of uricase;
(b) before the N-terminus of uricase;
(c) after the C-terminus of uricase; and
(d) any combinations of (a), (b) and (c) as mentioned above;
wherein the amino acid position is based on the uricase sequence as shown in SEQ ID NO.: 1.

In another preferred embodiment, the number of the recombinantly introduced cysteine residues is 1-4, preferably 1-3, more preferably 1-2, and most preferably 1.

In another preferred embodiment, the introduction of the recombinantly introduced cysteine residue includes substitution (displacement), insertion (at the non-end), and/or addition (at the N-terminus or C-terminus).

In another preferred embodiment, the inactive region is a region of uricase selected from a group consisting of: positions 103±1, 148±1, 177±1, 202±1, 228±1, and 291±1; more preferably, positions 103, 148, 177, 202, 228, and 291 of uricase.

In another preferred embodiment, the recombinantly introduced cysteine residue is introduced by substitution (or replacement).

In another preferred embodiment, the replaced original amino acid is selected from a group consisting of: K, N, Q, G, or a combination thereof.

In another preferred embodiment, the replaced original amino acid is selected from a group consisting of: lysine at position 103, asparagine at position 148, glutamine at position 177, glycine at position 202, lysine at position 228, lysine at position 291, and a combination thereof.

In another preferred embodiment, the recombinantly introduced cysteine residue is located at the N-terminus.

In another preferred embodiment, the recombinantly introduced cysteine residue is located at the C-terminus.

In another preferred embodiment, the recombinantly introduced cysteine residue is selected from a group consisting of: K103C, N148C, G202C, K228C, K291C, and a combination thereof.

In another preferred embodiment, the "inactive region" refers to a region where the activity of uricase is not substantially affected, i.e., after the inactive region is mutated, the formed mutant uricase still retains at least 70% (e.g., 70-200%, preferably 80-150%, more preferably 90-140%) of wild-type uricase activity.

In another aspect, the present invention also provides a derivative polypeptide of the above mutant uricase. The derivative polypeptide may also have a substitution, deletion or addition of one or several amino acid residues (preferably 1-20, more preferably 1-15, more preferably 1-10, more preferably 1-3, most preferably 1) based on the above mutant uricase, and the derivative polypeptide has the uricase activity.

In another preferred embodiment, the mutant uricase has an activity retention rate of ≥70%, preferably 80 to 200%, and more preferably 100 to 150%.

In another preferred embodiment, the mutant uricase has an average specific activity of ≥10 U/mg, preferably 12-30 U/mg, and more preferably 15-25 U/mg.

In another preferred embodiment, the mutant uricase is formed by mutation of the uricase as shown in SEQ ID NO.: 1.

In another preferred embodiment, the recombinantly introduced cysteine residue in the amino acid sequence as shown in SEQ ID NO.: 1 is selected from a group consisting of: K103C, N148C, G202C, K228C, K291C, and a combination thereof.

In the second aspect of the present invention, an isolated polynucleotide is provided, which encodes the mutant uricase according to the first aspect of the present invention.

In another preferred embodiment, the amino acid sequence of the mutant uricase encoded by the polynucleotide is shown in SEQ ID NO.: 1 and further contains a recombinantly introduced cysteine residue selected from a group consisting of: K103C, N148C, G202C, K228C, K291C, and a combination thereof.

In another preferred embodiment, the polynucleotide further comprises an auxiliary element selected from a group consisting of: a signal peptide, a secretory peptide, a tag sequence (e.g., 6His), and a combination thereof in the flank of the ORF of the mutant uricase.

In another preferred embodiment, the polynucleotide encodes a mutant uricase with an amino acid sequence as shown in SEQ ID NO.: 2.

In another preferred embodiment, the sequence of the polynucleotide is shown in SEQ ID NO.: 3.

In another preferred embodiment, the polynucleotide is selected from a group consisting of: a DNA sequence, and a RNA sequence.

In the third aspect of the present invention, a vector is provided, which comprises the polynucleotide according to the second aspect of the present invention.

In the fourth aspect of the present invention, a host cell is provided, which comprises the vector according to the third aspect of the present invention or has the polynucleotide of the second aspect of the present invention integrated into the genome.

In the fifth aspect of the present invention, a method for producing a mutant uricase according to the first aspect of the present invention is provided, which comprises the steps of:

Cultivating a host cell according to the fourth aspect of the present invention under conditions suitable for expression, thereby expressing the mutant uricase according to the first aspect of the present invention; and Isolating the mutant uricase.

In the sixth aspect of the present invention, a PEGylated mutant uricase is provided, the mutant uricase is the mutant uricase according to the first aspect of the present invention, and the PEGylation site is the position of the recombinantly introduced cysteine residue.

In another preferred embodiment, in the pegylated mutant uricase, PEG is modified by the targeted modification.

In another preferred embodiment, the targeted modification refers to recombinant introduction of cysteine residue at a site, preferably selected from a group consisting of: K103C, N148C, G202C, K228C, K291C, and a combination thereof.

In another preferred embodiment, in the pegylated mutant uricase, the number of PEGylated sites is 1-4, preferably 1-3, and more preferably 1-2.

In another preferred embodiment, the PEGylation is formed by reacting with a maleimide-type PEG molecule.

In another preferred embodiment, the molecular weight of maleimide-type PEG molecule is 10-40 KDa, preferably 15-30 KDa.

In another preferred embodiment, the mutant uricase comprises a monomer, or a tetramer form.

In another preferred embodiment, the molecular weight of PEGylated mutant uricase (monomer) is 45,000-80,000 Da, preferably 50,000-70,000 Da.

In another preferred embodiment, the molecular weight of PEGylated mutant uricase (tetramer) is 160,000-240,000 Da, preferably 180,000-200,000 Da.

In another preferred embodiment, in the pegylated mutant uricase, the PEGylation ratio in the recombinantly introduced cysteine residue sites is 50-100% (mole), preferably 60-90% (mole).

In another preferred embodiment, the PEG is coupled to the recombinantly introduced cysteine residue through a chemical bond (e.g., a covalent bond).

In another preferred embodiment, the half-life of the pegylated mutant uricase is ≥72 hours, preferably 80-120 hours, more preferably 90-110 hours. In another preferred embodiment, the enzyme specific activity of pegylated mutant uricase is ≥10 U/mg, preferably 15 U/mg.

In another preferred embodiment, the pegylated mutant uricase has one or more of following characteristics:

(i) exhibiting enzyme activity at pH 6-10 (preferably the enzyme activity at said pH is at least 50% of the highest enzyme activity);

(ii) exhibiting enzyme activity at 5° C. to 45° C. (preferably the enzyme activity at said temperature is at least 30% of the highest enzyme activity).

In the seventh aspect of the present invention, a pharmaceutical composition is provided, which comprises:

the pegylated mutant uricase according to the sixth aspect of the invention; and a pharmaceutically acceptable carrier.

In another preferred embodiment, the pharmaceutical composition is a liquid formulation.

In another preferred embodiment, the pharmaceutical composition is an injection, a lyophilized formulation.

In the eighth aspect of the present invention, a use of the mutant uricase according to the first aspect of the present invention, the pegylated mutant uricase according to the sixth aspect of the present invention and the pharmaceutical composition according to the seventh aspect of the present invention is provided for preparing a drug for the treatment of gout and/or reduction of uric acid levels.

In the ninth aspect of the present invention, a method for preparing the pegylated mutant uricase according to the sixth aspect of the present invention is provided, which comprises the steps of:

(i) providing a mutant uricase according to the first aspect of the present invention;

(ii) the mutant uricase of step (i) is subjected to a PEGylation treatment, thereby forming the pegylated mutant uricase according to the sixth aspect of the invention.

In another preferred embodiment, in step (ii), the PEGylation treatment comprises performing PEGylation reaction with polyethylene glycol (mPEG-Ala-MAL) having a maleimide active group.

In another preferred embodiment, in step (ii), the PEGylation treatment is performed at 20-30° C.

In another preferred embodiment, in step (ii), the PEGylation treatment is performed for 0.5-3 hours.

In another preferred embodiment, after step (ii), a step of isolating and/or purifying the formed pegylated mutant uricase is further included.

In the tenth aspect of the present invention, a non-therapeutic method for reducing the level of uric acid in a mammal's body fluid or tissue is provided, which comprises the steps of:

administering to a subject the pegylated mutant uricase according to the sixth aspect of the present invention; and detecting the level of uric acid in the body fluid or tissue of the subject.

In another preferred embodiment, the subject comprises a non-human mammal.

In another preferred embodiment, the subject comprises a rodent, including a rat and a mouse.

In another preferred embodiment, the administration method comprises an intravenous injection, an intraperitoneal injection, a subcutaneous injection.

It should be understood that, within the scope of the present invention, the technical features specifically described above and below (such as the Examples) can be combined with each other, thereby constituting a new or preferred technical solution which needs not be described one by one.

DESCRIPTION OF DRAWINGS

FIG. 1 shows a site-directed mutated location diagram in a three-dimensional, stereo simulation structure of a wild-type uricase wherein, FIG. 1A is a lateral view; FIG. 1B is an apical view.

DETAILED DESCRIPTION OF INVENTION

Figure 1:
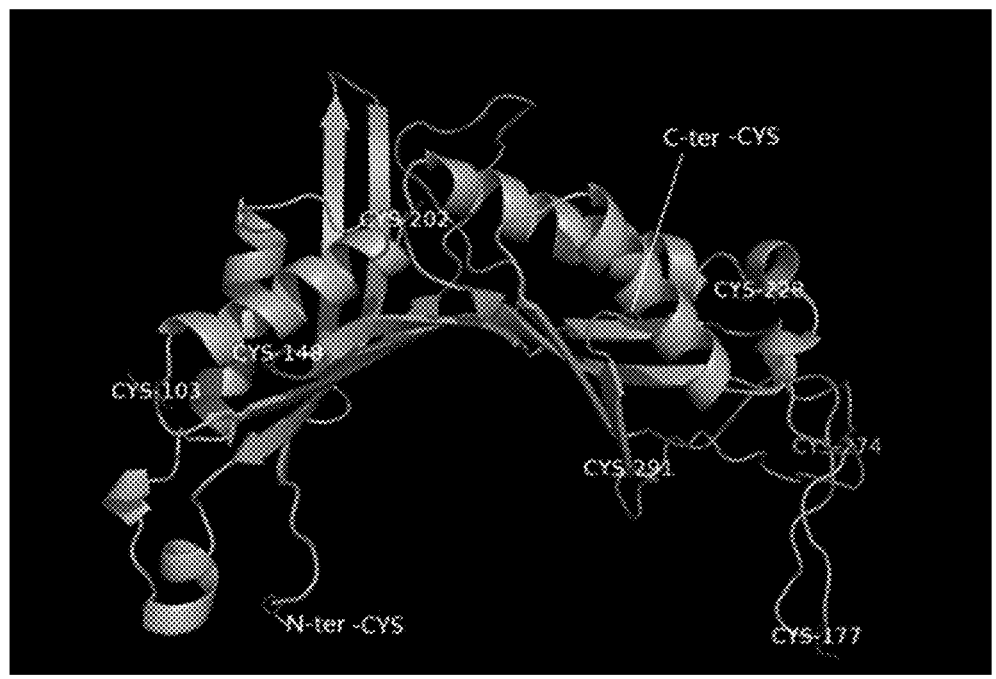
Figure 1:
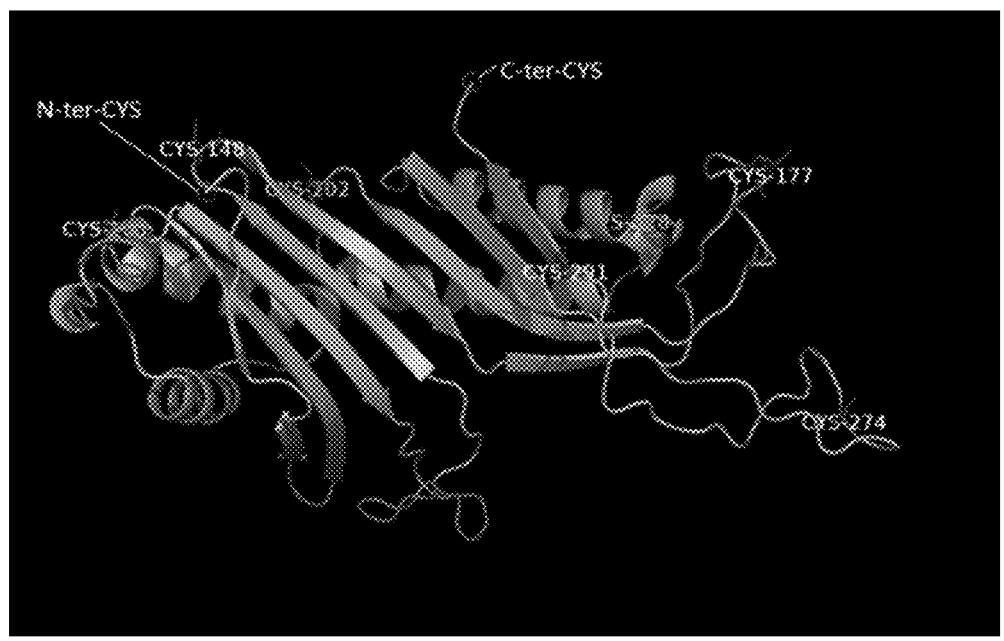

After extensive and intensive researches, the inventors have unexpectedly found that although a wild-type uricase has multiple cysteine sites, it can not be effectively PEGylated, and if a cysteine is artificially introduced in a specific position (such as, an inactive region, a N-terminus and/or a C-terminus) of a recombinant uricase, the resulting uricase mutant can retain more than 70% of uricase activity (even with an increase in activity), and after the above uricase mutants are PEG site-directed modified, the resulting PEGylated uricase mutants have characteristics, such as longer half-life, homogenization of the product, and more stable enzyme activity. Based on the above findings, the present invention is completed.

Terms

As used herein, the terms "mutant type uricase", "mutant uricase" and "uricase mutant" can be used interchangeably and all refer to a mutant protein of the first aspect of the present invention which incorporates a cysteine residue and retains the uricase activity. The recombination introduction of cysteine is a site-directed introduction, and in particular, a cysteine is introduced at the N-terminus, C-terminus of a uricase, or the inactive region of a uricase. Uricase, after introduction of cysteine (i.e., the mutant uricase) still retains at least 70% (e.g., 70-200%, preferably 80-150%, and more preferably 90-140%) of the activity of a wild-type uricase.

The present invention also provides a derivative polypeptide of the mutant uricase as described above, which may further have a substitution, a deletion or an addition of one or several amino acid residues (preferably 1-20, more preferably 1-15, more preferably 1-3, most preferably 1) based on the mutant uricase as described above, and the derivative polypeptide possesses the uricase activity.

As used herein, the "PEG" refers to polyethylene glycol, and specifically refers to a mixture of ethylene oxide polycondensate and water, represented by the general formula $H(OCH_2CH_2)_n$—OH, wherein $n \geq 4$. Typically, the molecular weight of a PEG molecule is $\geq 5$ KDa, preferably 10-40 KDa, more preferably 15-30 KDa.

The Starting Uricase

In the present invention, the uricase used as a starting uricase is not particularly limited and may be a uricase of any source. Representative examples include, but are not limited to, a mammalian uricase, a recombinant uricase. In addition, the starting uricase may be either a wild-type uricase or a mutant uricase containing a mutation.

A preferred starting uricase is a chimeric protein comprising two or more mammalian amino acid sequences, such as a recombinant uricase comprising segments of a pig uricase and a baboon uricase.

In another preferred embodiment, the N-terminus of the starting uricase is derived from a pig uricase and the C-terminus is derived from a baboon uricase. More preferably, the N-terminus of the starting uricase is derived from 225 amino acids of the pig uricase and the C-terminus is derived from 79 amino acids of the baboon uricase.

The amino acid sequence of a typical starting uricase is shown in SEQ ID NO.: 1.

Preparation of the Mutant Uricase

A full length nucleotide sequence of the mutant uricase of the present invention or a fragment thereof can generally be obtained by a PCR amplification method, a recombinant method or an artificial synthetic method. For a PCR amplification method, primers can be designed according to the relevant nucleotide sequences disclosed in the present invention, particularly the open reading frame sequences, and the commercially available cDNA libraries or cDNA libraries prepared by the conventional methods known to the skilled in the art were used as a template, and amplified and the relevant sequences were obtained. When the sequence is relatively long, two or more PCR amplifications are usually needed, and then each of the amplified fragments are spliced together in the correct order.

Once the relevant sequence is obtained, the relevant sequence can be obtained in bulk using a recombination method. Usually the sequence is cloned into a vector, and then transferred into a cell, and then the relevant sequence is separated and obtained from the proliferation of host cells by a conventional method.

In addition, the relevant sequence can also be synthesized using artificial synthesis methods, particularly when the fragment is relatively short. In general, a very long fragment can be obtained by firstly synthesizing multiple small fragments and then ligating them.

At present, a DNA sequence encoding the protein of the present invention (or fragments thereof, or derivatives thereof) can completely be obtained by chemical synthesis. The DNA sequence can then be introduced into a variety of existing DNA molecules (or vectors) and cells known in the art. In addition, mutations can also be introduced into the protein sequences of the present invention by chemical synthesis.

The present invention also relates to a vector containing a polynucleotide of the present invention, and a host cell produced by genetic engineering using a vector or a mutant uricase encoding sequence of the present invention, and a method for producing the polypeptide of the present invention by recombinant techniques.

With the conventional recombinant DNA technique (Science, 1984; 224: 1431), the polynucleotide of the present invention can be used to express or produce the mutant uricase polypeptide. Generally, the method comprises the following steps:

(1) Transforming or transfecting a suitable host cell with a polynucleotide (or variant) encoding the mutant uricase polypeptide of the present invention or a recombinant expression vector containing said polynucleotide;

(2) Culturing the host cell in a suitable culture medium;

(3) Isolating and purifying protein from the culture medium or cell.

Transformation of host cells with recombinant DNA can be carried out using conventional techniques well known to the skilled in the art. When the host is a prokaryote such as *E. coli* (e.g., *E. coli* BL21(DE3)pLysS, BL21(DE3)), competent cells capable of absorbing DNA can be harvested after the exponential growth phase and treated with $CaCl_2$, the steps used are well known in the art. Another method is to use $MgCl_2$. If necessary, the transformation can also be carried out by means of electroporation. When the host is an eukaryote, the following DNA transfection methods are available: calcium phosphate coprecipitation, conventional mechanical methods such as microinjection, electroporation, liposome packaging, and the like.

The obtained transformants can be cultured by a conventional method to express a polypeptide encoded by a gene of the present invention. According to the host cell used, the medium used in the culture may be selected from a variety of conventional media. And the host cell can be cultured under conditions suitable for the growth of the host cell. After the host cell grows to the appropriate cell density, the selected promoter is induced with a suitable method, such as temperature conversion or chemical induction, and the cells are incubated for a further period of time.

The recombinant polypeptide in the method above may be included in the cells, or expressed on the cell membrane, or secreted out of the cell. If desired, the physical, chemical and other properties can be utilized in various isolation methods to isolate and purify the recombinant protein. These methods are well-known to those skilled in the art. The examples of these methods include, but are not limited to, conventional renaturation treatment, treatment by protein precipitant (such as salt precipitation), centrifugation, cell lysis by osmosis, sonication, supercentrifugation, molecular sieve chromatography (gel chromatography), adsorption chromatography, ion exchange chromatography, high performance liquid chromatography (HPLC), and any other liquid chromatography, and the combinations thereof.

The amino acid sequence of a typical mutant uricase is shown in SEQ ID NO.: 2.

The nucleotide sequence of a typical mutant uricase is shown in SEQ ID NO.: 3.

PEGylated Mutant Uricase

Mutant uricases can be covalently bound to PEG via chemical bonds using methods known in the art. In general, PEG may bind to a mutant uricase through a linking group, wherein the linking group may be selected from a group consisting of: succinimidyl, acylamino, imide groups, carbamate, ester groups, epoxy groups, carboxyl groups, hydroxyl groups, carbohydrate groups, tyrosine groups, cysteine groups, histidine groups, and combinations thereof. In addition, mutant uricases can also be directly coupled to PEG via amino, sulfhydryl, hydroxyl, or carboxyl groups (i.e., no linking groups).

In a preferred embodiment of the present invention, PEG is coupled via a chemical bond (e.g., a covalent bond) to a recombinantly introduced cysteine residue on a mutant uricase.

In a preferred embodiment of the present invention, PEG is site-directed modified. Mutant uricases can be monomeric or tetrameric. The enzyme may be covalently bound to 1 to 4, preferably 1 to 3, more preferably 1 to 2 PEG (s). These PEGs can be linear or branched.

The molecular weight of a preferred pegylated mutant uricase (tetramer) is 160,000-220,000 Da.

Pharmaceutical Compositions

The present invention also provides a pharmaceutical composition comprising an effective amount of a pegylated mutant uricase of the present invention and a pharmaceutically acceptable carrier. In general, the pegylated mutant uricase of the present invention can be formulated in a non-toxic, inert, and pharmaceutically acceptable aqueous carrier media, wherein the pH is generally about 5-8, preferably, about 6-8.

As used herein, the term "effective amount" or "effective dose" refers to an amount that can produce a function or activity for humans and/or animals and that can be accepted by humans and/or animals, such as 0.001-99 wt %; preferably 0.01-95 wt %; more preferably, 0.1-90 wt %.

As used herein, a "pharmaceutically acceptable" ingredient is a substance that is suitable for humans and/or mammals without undue adverse side effects (such as toxicity, irritation, and allergic reaction), i.e., which has a reasonable benefit/risk ratio. The term "pharmaceutically acceptable carrier" refers to a carrier for the administration of a therapeutic agent, including various excipients and diluents.

The pharmaceutical composition of the present invention contains a safe and effective amount of the pegylated mutant uricase of the present invention and a pharmaceutically acceptable carrier. Such carriers include, but are not limited to, saline, buffer, glucose, water, glycerol, ethanol, and combinations thereof. In general, the pharmaceutical preparation should be matched with the administration method, and the pharmaceutical composition of the present invention can be prepared as an injection, for example, prepared by a conventional method using a physiological saline or an aqueous solution containing glucose and other adjuvants. The pharmaceutical composition is preferably manufactured under aseptic conditions. The administration dosage of active ingredient is a therapeutically effective amount. The pharmaceutical preparation of the present invention can also be made into a sustained-release preparation.

The effective amount of the pegylated mutant uricase of the present invention may vary depending on the mode of administration and the severity of the disease to be treated. The choice of preferred effective amount can be determined by one of ordinary skill in the art based on various factors (e.g., by clinical trials). Such factors include, but are not limited to, the pharmacokinetic parameters of the pegylated mutant uricase of the present invention such as bioavailability, metabolism, half-life, etc.; the severity of the disease to be treated by the patient, the weight of the patient, and the patient's immunity status, route of administration, etc. For patients with high uric acid levels, in general, when the PEGylated mutant uricase of the present invention is administered at a dose of about 0.5 mg to 100 mg/kg animal body weight (preferably 1 mg to 50 mg/kg animal body weight) per day, a satisfactory result can be obtained. For example, several separate doses may be administered daily, or the dose may be proportionally reduced, as urgent required by the therapeutic situation.

Prior to injection, the pegylated mutant uricase of the present invention may be mixed with a phosphate buffered saline solution or any other suitable solution known to those skilled in the art, and the pharmaceutical composition of the present invention may be administered as a lyophilate or a liquid formulation as desired.

A Method for Reducing Uric Acid Levels in Body Fluids or Tissues

In another preferred embodiment, the method comprises: ingesting the pharmaceutical composition of the present invention. The subject is human.

In another preferred embodiment, the method comprises: ingesting the pharmaceutical composition of the present invention. The subject is an animal, preferably a rat, a rabbit.

The main advantages of the present invention include:

(1) In the present invention, a cysteine is site-directed introduced into a uricase, and the mutant uricase formed after the introduction of the cysteine can retain at least 70% activity (e.g. 70-200%, preferably 80-150%, more preferably 90-140%) of a wild-type uricase.

(2) The cysteine residue in the mutant uricase of the present invention is coupled with PEG to obtain a pegylated mutant uricase. The PEG-modified mutant uricase has the following characteristics: an extended half-life, homogenization of the product, and a stable enzyme activity.

The present invention is further described below with reference to specific embodiments. It should be understood that these examples are only for illustrating the present invention and not intended to limit the scope of the present invention. The conditions of the experimental methods not specifically indicated in the following examples are usually in accordance with conventional conditions as described in Sambrook et al., Molecular Cloning: A Laboratory Manual (New York: Cold Spring Harbor Laboratory Press, 1989), or according to the conditions described in the Journal of Microbiology: An Experimental Handbook (edited by James Cappuccino and Natalie Sherman, Pearson Education Press) or the manufacturer's proposed conditions. Unless otherwise specified, percentages and parts are percentages by weight and parts by weight.

Unless otherwise specified, the materials used in the examples are all commercially available products, in which plasmids and *E. coli* are purchased from Novagen.

Example 1 Determination of the Mutation Site

After extensive analysis and researches, 8 mutation sites (site-directed mutation to Cys) were determined, of which 6 sites were exposed to the outside of the tetramer, and 2 sites were located at the C terminal and the N terminal (Table 1, FIG. 1).

TABLE 1

Selection of different mutation sites and the amino acids replaced by cysteine (Cys)

| No. | mutation position (monomer) | original animo acid |
|---|---|---|
| K103C | 103 | Lys |
| N148C | 148 | Asn |
| Q177C | 177 | Gln |
| G202C | 202 | Gly |
| K228C | 228 | Lys |
| K291C | 291 | Lys |
| N-ter-C | 0 | an Cys is introduced |
| C-ter-C | 305 | an Cys is introduced |

Example 2 Construction of Mutant Strains

2.1 Obtainment of the Mutant Gene

K291C, mutation at N terminal and C terminal were obtained by a method of full sequence synthesis, K103C, N148C, Q177C, G202C, K228C, G274C were obtained by duplex PCR, and the sequences of the primers were shown as follows:

TABLE 2 primer design for different mutation sequences

| Name of the Primer | Sequence (5'-3') | SEQ ID NO.: |
|---|---|---|
| PBC-F (containing a NcoI site) | GCATCCGATGACCCAAT<u>CCATGG</u>CT | 4 |
| PBC-R (containing a BamHI site) | ACCCAAT<u>GGATCC</u>TCATCACAGTCT | 5 |
| PBC-K103C-F | TTTCCTTTCTTCCTTC<u>TGT</u>CATGTCATCAGAGCTCA | 6 |
| PBC-K103C-R | TGAGCTCTGATGACATG<u>ACA</u>GAAGGAAGAAAGGAAA | 7 |
| PBC-N148C-F | GAGGTTGAACAGATAAGG<u>TGT</u>GGACCTCCAGTCATT | 8 |
| PBC-N148C-R | AATGACTGGAGGTCC<u>ACA</u>CCTTATCTGTTCAACCTC | 9 |
| PBC-Q177C-F | AAGGATTCATCAAGGAC<u>TGC</u>TTCACCACCCTCCTG | 10 |
| PBC-Q177C-R | CAGGGAGGGTGGTGAA<u>GCA</u>GTCCTTGATGAATCCTT | 11 |
| PBC-G202C-F | CGCTACCACCAG<u>TGC</u>AGAGATGTGGACTTTGA | 12 |
| PBC-G202C-R | TCAAAGTCCACATCTCT<u>GCA</u>CTGGTGGTAGCG | 13 |
| PBC-K228C-F | AATTTGCTGGGCCCTATGAC<u>TGT</u>GGCGAGTACTCA | 14 |
| PBC-K228C-R | TGAGTACTCGCC<u>ACA</u>GTCATAGGGCCCAGCAAATT | 15 |

2.2 Construction of the Expression Plasmid

Figure 2:
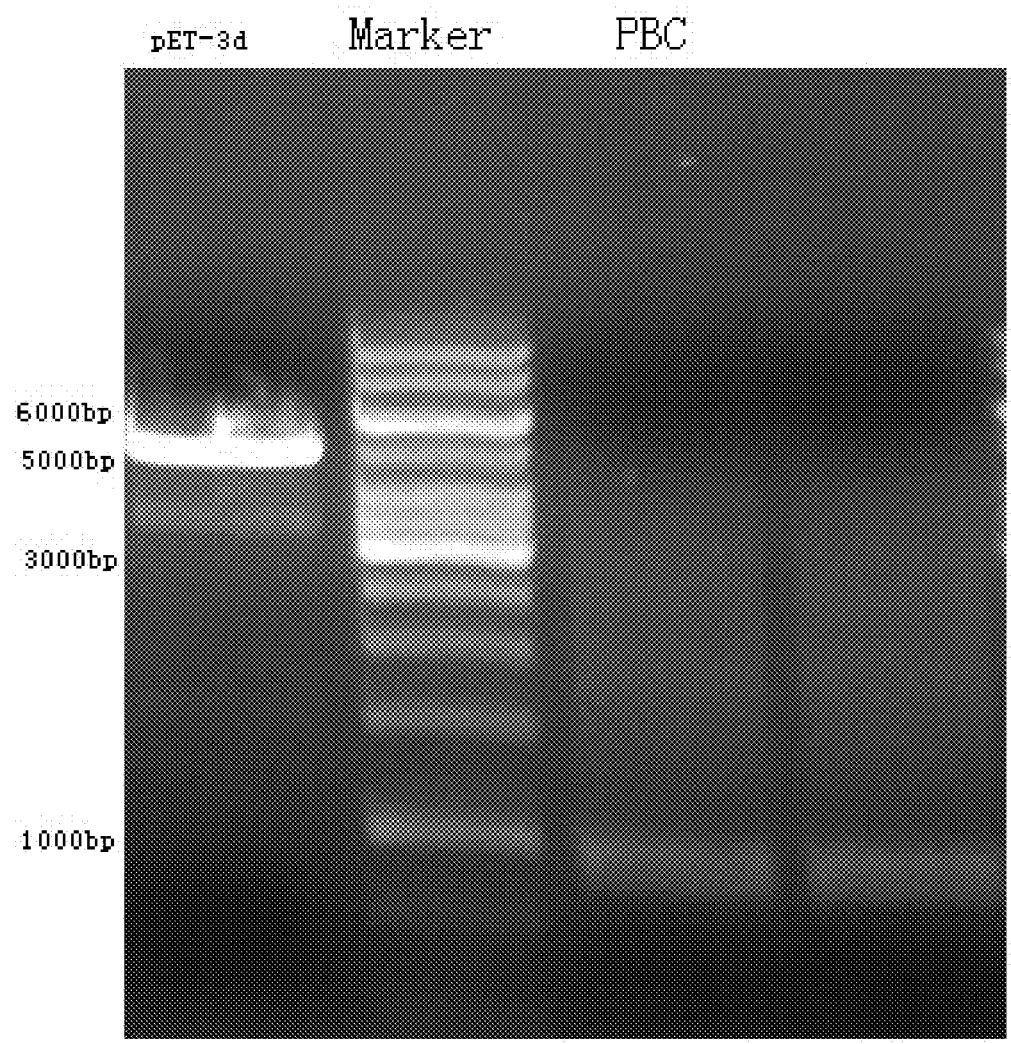
FIG. 2 shows the results of a electrophoresis of the vector plasmid pET3d and the target fragment mutant PBC double enzyme digested by NcoI and BamHI (the plasmid pET24d is not shown and the results are the same), wherein PBC represents the wild-type uricase of the present invention.

The plasmid pET3d (purchased from Novagen) or pET24d (purchased from Novagen) and a target fragment were subjected to a double-enzyme digestion, respectively (FIG. 2), recovered and ligated with a T4 ligase, all of the ligation products were added into 50 μL of freshly thawed common *Escherichia coli* (for example, DH5α competent cell), gently blended, placed in an ice-bath for 30 mins, heat-shocked at 42° C. for 90 s; and immediately placed in an ice-bath for 2 min; then 500 μL of a sterile LB medium was added and blended, cultured at 37° C., 200 rpm for 1 h for rendering the bacteria recover, coated on the plate containing the corresponding resistance; monoclonal colonies were selected; and the successfully transformed strains were identified by PCR.

2.3 Construction of the Mutant Strains

Figure 3A:
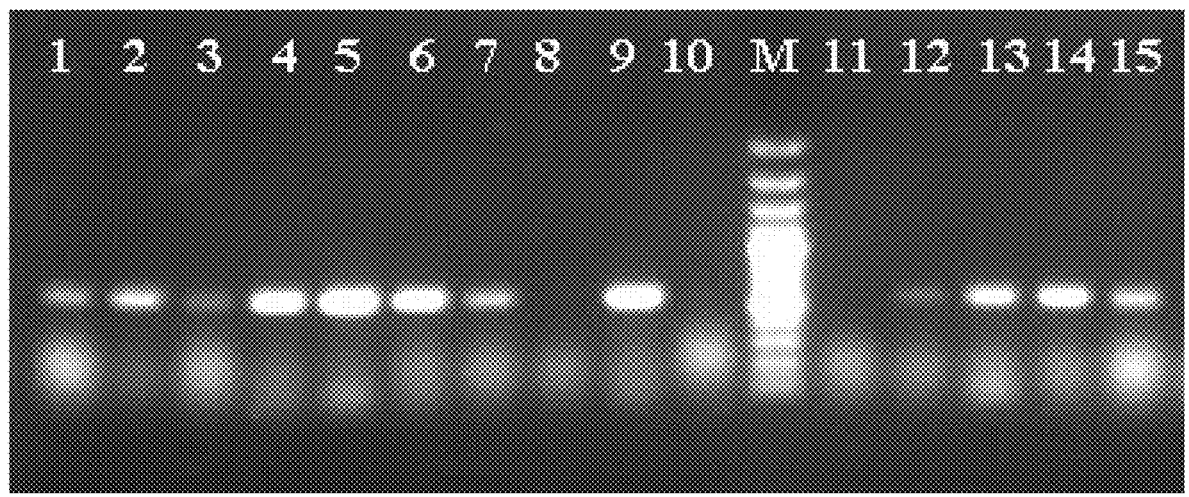
FIG. 3a shows a PCR identification chart of multiple mutants with mutation points within the sequence. Wherein: 1, 2: K103C; 3, 4: N148C; 5, 6: Q177C; 7, 8: G202C; 9, 10: K228C; M: Marker (molecular weight standard); 11: negative control (NC); 13: G274C; 14, 15: K291C.
Figure 3B:
FIG. 3b shows a PCR identification chart of 2 mutants with the mutation points at the end of the sequence. Wherein, 1-3: N-ter-C; 4-6: C-ter-C; M: Marker (molecular weight standard).

The plasmid was extracted, the plasmids that were correctly sequenced as described above were transformed into *E. coli* BL21(DE3)pLysS (purchased from Novagen) and BL21(DE3) (purchased from Novagen) respectively to construct expression strains (mutant strains), and the mutant strains were identified by PCR (FIG. 3a and FIG. 3b).

Example 3 Expression of Mutant Uricase and Determination of its Activity

Figure 4A:
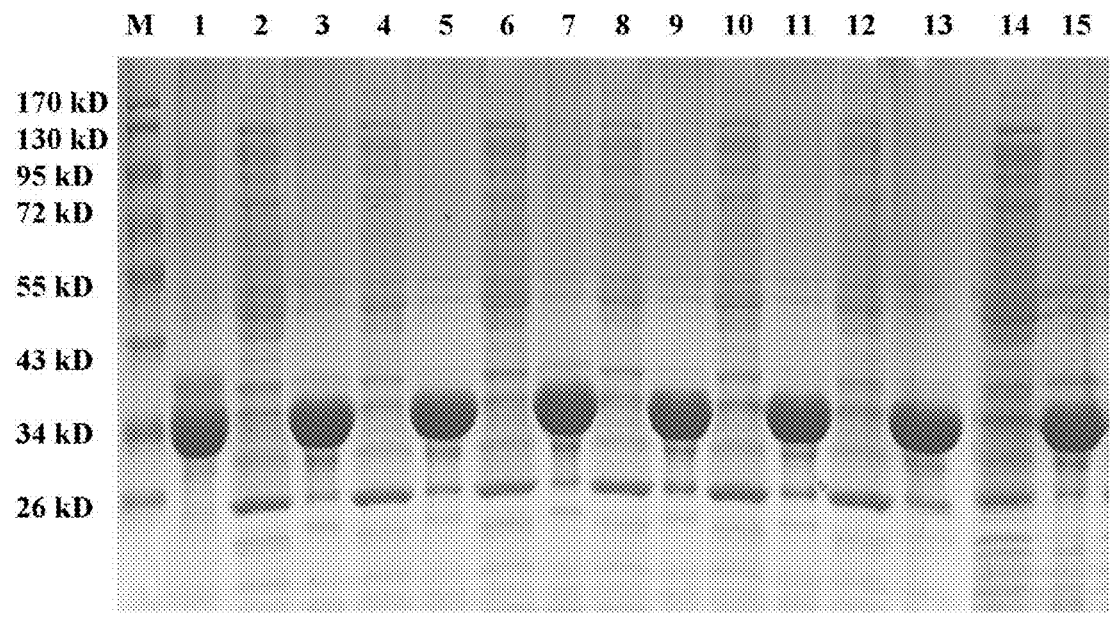
FIG. 4a shows that after the seven mutants with the mutation points within the sequence were induced by IPTG, the expression of the recombinant protein is identified by SDS-PAGE. Wherein, M: Marker (molecular weight standard); 1: precipitation of wild type PBC; 2: K103C supernatant; 3: K103C precipitation; 4: N148C supernatant; 5: N148C precipitation; 6: Q177C supernatant; 7: Q177C precipitation; 8: G202C supernatant; 9: G202C precipitate; 10: K228C supernatant; 11: K228C precipitation; 12: G274C supernatant; 13: G274C precipitation; 14: K291C supernatant; 15: K291C precipitation. Wherein, the molecular weight of the expressed uricase protein (monomer) is about 35 Kda.
Figure 4B:
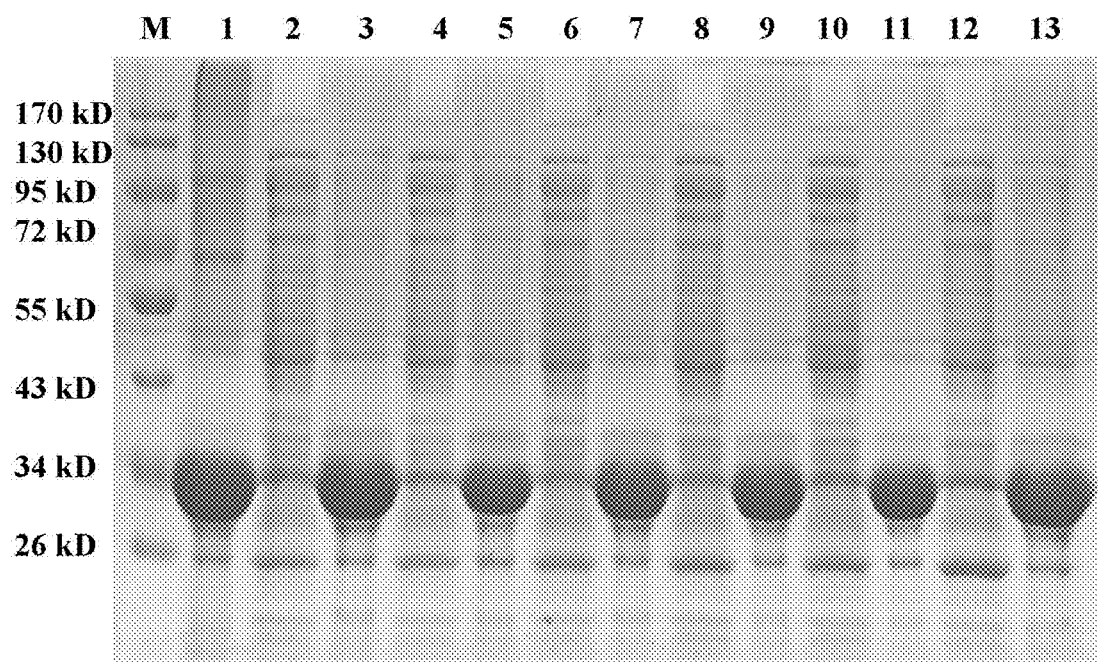
FIG. 4b shows that after the two mutants with the mutation points at the end of the sequence was induced by IPTG, the expression of the recombinant protein is identified by SDS-PAGE. Wherein, M: Marker (molecular weight standard); 1: precipitation of a wild-type PBC; 2, 4, 6: N-ter-C supernatant; 3, 5, 7: N-ter-C precipitation; 8, 10, 12: C-ter-C supernatant; 9, 11, 13: C-ter-C precipitation. Wherein the molecular weight of the expressed uricase protein (monomer) is about 35 Kda.

BL21(DE3)pLysS-pET3d-PBC-C grown on Amp and Chl double-antibody plate and BL21(DE3)-pET24d-PBC-C grown on Kan monoclonal antibody plate were activated in 5 ml of tubes, respectively, overnight at 37° C., 220 rpm, transferred to 100 ml of shake flasks, shaked for 2 h at 37° C., 220 rpm, to OD600 of about 0.6; IPTG was added for the induction overnight at 28° C., 220 rpm; the supernatant was removed by centrifugation at 8000 rpm and the bacteria was collected; the bacteria was resuspended in 1/10 volume of the bacteria liquid, and then was subjected to supersonic treatment over 5 s at 20 kHz, then stopped for 5 s until completely crushed, separated by centrifugation, the supernatant and precipitate after broken were detected by SDS-PAGE electrophoresis (FIG. 4a and FIG. 4b); after the above precipitate was resuspended and rinsed once with an equal volume of PBS, the precipitate was obtained by centrifugation at 12000 rpm for 10 min, and dissolved in 0.1M, pH 10.12 of CBS, and the supernatant was obtained by centrifugation at 12000 rpm for 10 min and used as a enzyme crude extract.

The activity of uricase was detected by UV spectrophotometry, enzymatic reaction rate was detected by measuring the decrease in absorbance at 290 nm caused by the oxidation of uric acid to allantoin. The enzyme activity unit is defined as follows: at 37° C., pH 8.5, the amount of uricase needed to catalyze the decomposition of 1 μmol of uric acid per minute is defined as 1 enzyme activity unit. The efficacy of uricase is represented as the activity unit of protein per mg (U/mg). Through preliminary experiments, the absorption spectrum of uricase has been scanned and showed a maximum absorption peak at 290 nm, and the extinction coefficient of 1 mM uric acid at 290 nm was 12.04 mM-1 cm-1. Therefore, the oxidation of 1 μM uric acid in the reaction caused the reduction of absorbance by 12.04 mAu. The absorbance is derived from the linear part as the changes of the uric acid concentration. Wherein the calculation formula of enzyme activity is shown as follows:

Enzyme activity (U/ml)=$(OD_b-OD_t)*V_t*df/12.04*1.0*V_s*t$ ($Od_b$: the absorbance value in a blank control tube; $Od_t$: the absorbance value in a detection tube; Vt: the total reaction volume, 1.28 ml; df: the dilution fold before sample addition to the system; Vs: the total volume after adding the test sample of uricase, 0.2 ml; t: the reaction time, 5 min; 12.04: the molar extinction coefficient of the substrate, uric acid under the test conditions; 1.0: optical path of cuvette, 1.0 cm)

Enzyme activity (U/mg)=(U/ml)/C (C: enzyme concentration, mg/ml)
Determination Method of the Activity:

(1) 1 mL of uric acid working solution was added to 2 EP tubes, respectively, marked as a reaction tube and a control tube, and subjected to the warm bath at 37° C. for 5 mins;

(2) Reaction tube: 200 μL of diluted enzyme solution was added at 37° C., and reacted for 5 min; control tube: no treatment at 37° C. and reacted for 5 min;

(3) Reaction tube: 80 μL, 20% of KOH was added to quench the reaction; control tube: after 80 μL, 20% of KOH was added to quench the reaction, 200 μL of diluted enzyme solution was added;

(4) UV absorption wavelength was determined at 290 nm.

The results were shown in Table 3. The results showed that after the *E. coli* was induced to express the mutant uricase, the activity retention and protein concentration of the mutant strains K103C and K291C exhibited a significant advantage.

TABLE 3

Protein extraction concentration and activity of recombinant uricase of different mutants

| No. | activity retention ratio | average protein concentration mg/mL | average specific activity of enzyme U/mg |
|---|---|---|---|
| K103C | 104% | 3.09 | 12.82 |
| N148C | 125% | 2.87 | 17.11 |
| Q177C | 88% | 3.47 | 16.44 |
| G202C | 114% | 3.25 | 22.23 |
| K228C | 148% | 4.08 | 16.37 |
| K291C | 111% | 3.45 | 15.98 |
| N-ter-C | 133% | 1.63 | 20.11 |
| C-ter-C | 108% | 2.05 | 12.07 |

Note:
"-ter-" represents terminal.

Wherein N-ter-C represents that a Cys is added at N terminal, whereas C-ter-C represents that a Cys is added at C terminal.

Example 4 PEG Modification for the Mutant Uricase

PBC of different mutants was formulated to a concentration of 2 mg/ml, with a molar ratio to MAL-mPEG (maleimide-type PEG, with a molecular weight of approximately 20 kD) of 1:2, a final reaction protein concentration of 1 mg/ml, pH 7, reacted at room temperature for 2 h, and the electrophoresis detection was performed.

Figure 5A:
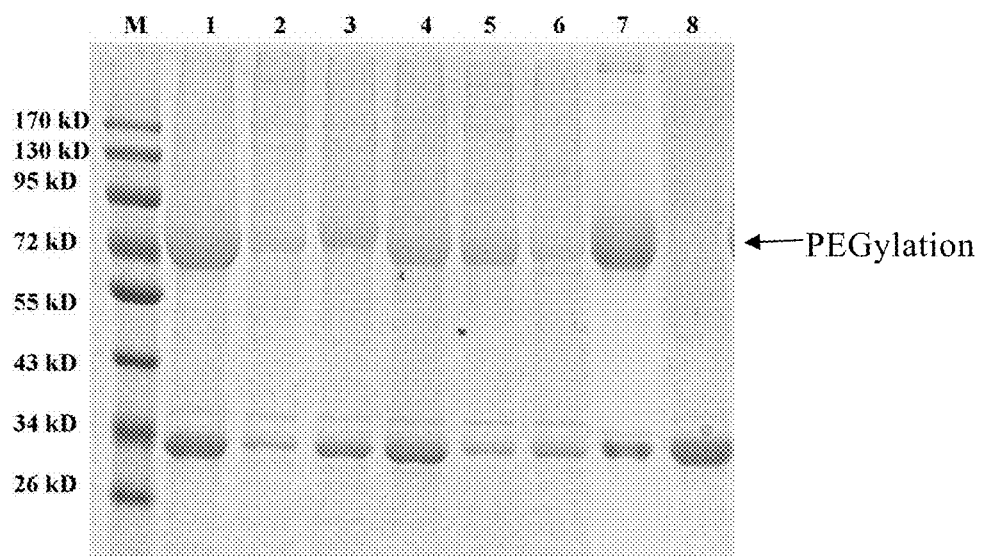
FIG. 5a shows a SDS-PAGE identification result of multiple recombinant uricase and wild-type uricase proteins with mutation points within the sequence modified by PEG. Wherein, M: Marker (molecular weight standard); 1: mPEG-K103C; 2: mPEG-N148C; 3: mPEG-Q177C; 4: mPEG-G202C; 5: mPEG-G274C; 6: mPEG-K291C; 7: mPEG-K228C; 8: mPEG-PBC (a wild-type uricase protein).
Figure 5B:
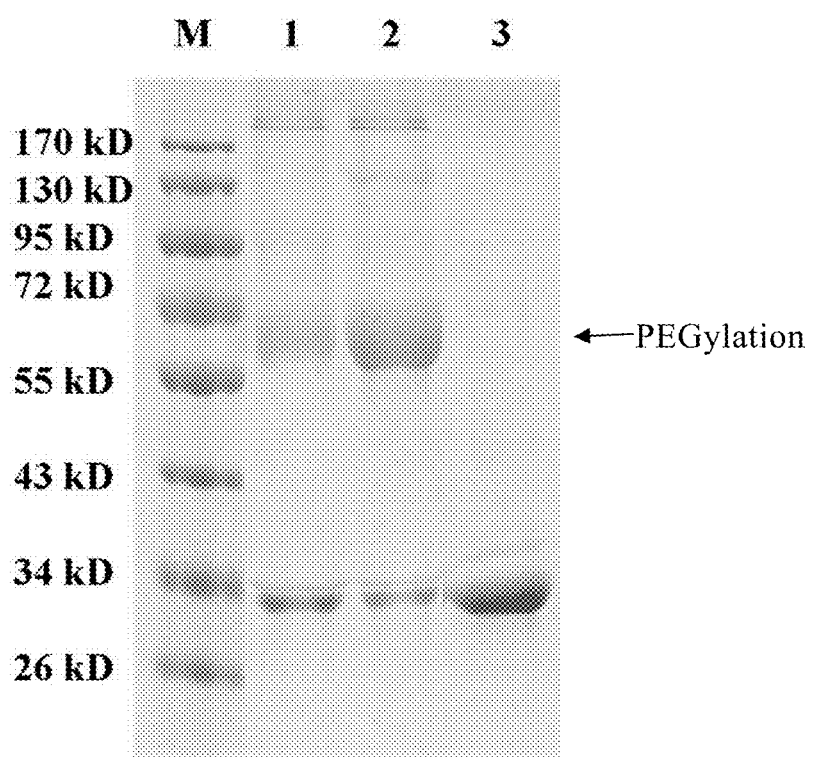
FIG. 5b shows a SDS-PAGE identification result of two recombinant uricase and wild-type uricase proteins with mutation points at the end of the sequence modified by PEG. Wherein, M: Marker (molecular weight standard); 1: mPEG-C-ter-C; 2: mPEG-N-ter-C; 3: mPEG-PBC (a wild-type uricase protein).

The results were shown in FIGS. 5a and 5b. The results showed that the unmutated wild-type uricase could not be pegylated (lane 8 in FIG. 5a and lane 3 in FIG. 5b), whereas each mutant uricase after site-directed mutagenesis could be PEGylated, wherein the K103C mutant has the highest modification efficiency.

K103C mutant was taken as an example. After PEGylation, the molecular weight of K103C monomer was 35 Kda, and the molecular weight of a PEG molecule was 20 Kda. Due to the hydration of the PEG molecule, the actual apparent molecular weight could be increased by approximately 1.5-2.5 times. Therefore, after PEGylation, the molecular weight of the uricase monomer will be about 65-85 kDa. The actual experiments showed that there was a protein band at a position of about 70 kDa, indicating that this band was a pegylated uricase monomer (FIG. 5a).

The mutant with a Cys added at N-terminal was taken as an example. After PEGylation, the molecular weight was about 65-85 Kda. The band at about 70 Kda in the figure was a PEG-modified monomer uricase, which showed that the enzyme added with Cys can be modified by PEG. (FIG. 5b)

On a molar basis, one mole of the mutant uricase was modified by about 0.5-0.8 moles of PEG on average.

Example 5 Determination of Properties for the PEG-Modified Mutant Strain K103C (PEG-K103C)

5.1 Determination of Stability pH stability: the mutant uricases, K103C and PEG-K103C were formulated into solutions with the same concentration, pH was adjusted to 5, 6, 7, 8, 9, 10, and the enzyme activity was determined after placed for 2 h.

Temperature stability: the mutant uricases, K103C and PEG-K103C were placed at 4° C., 20° C., 37° C., 50° C., 60° C. for 2 h, and the enzyme activity was then determined.

Figure 6:
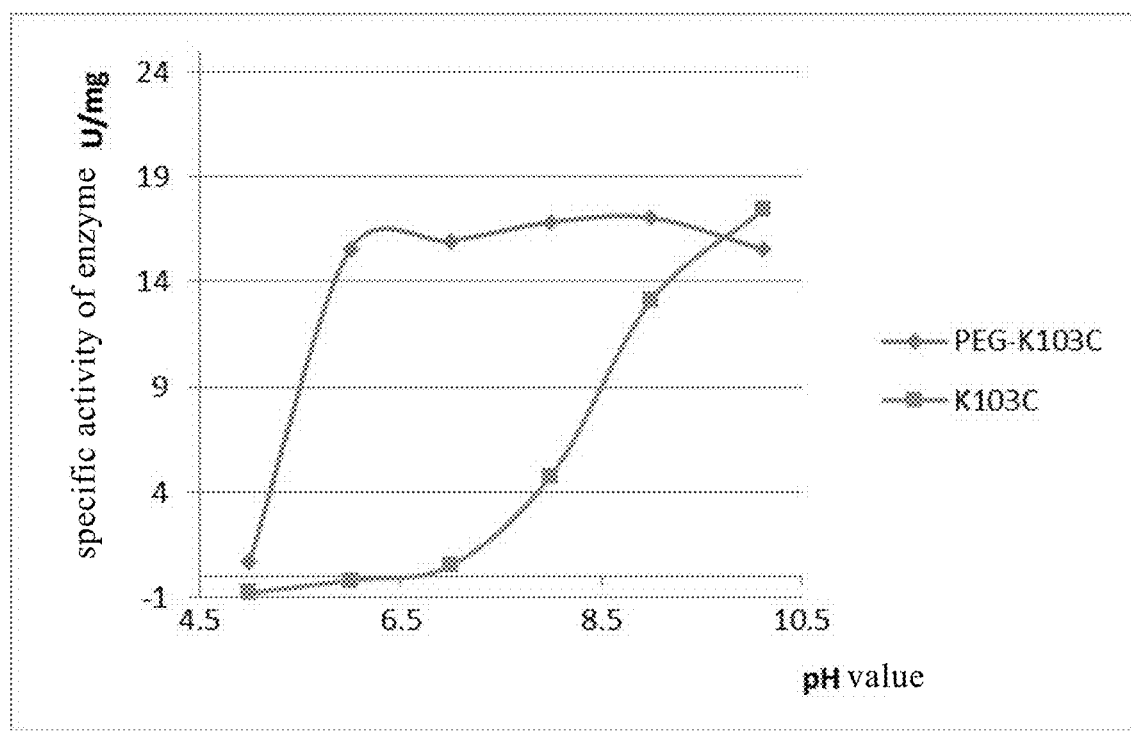
FIG. 6 shows a comparison result of pH stability between a PEG-modified recombinant uricase PEG-K103C and an unmodified K103C.
Figure 7:
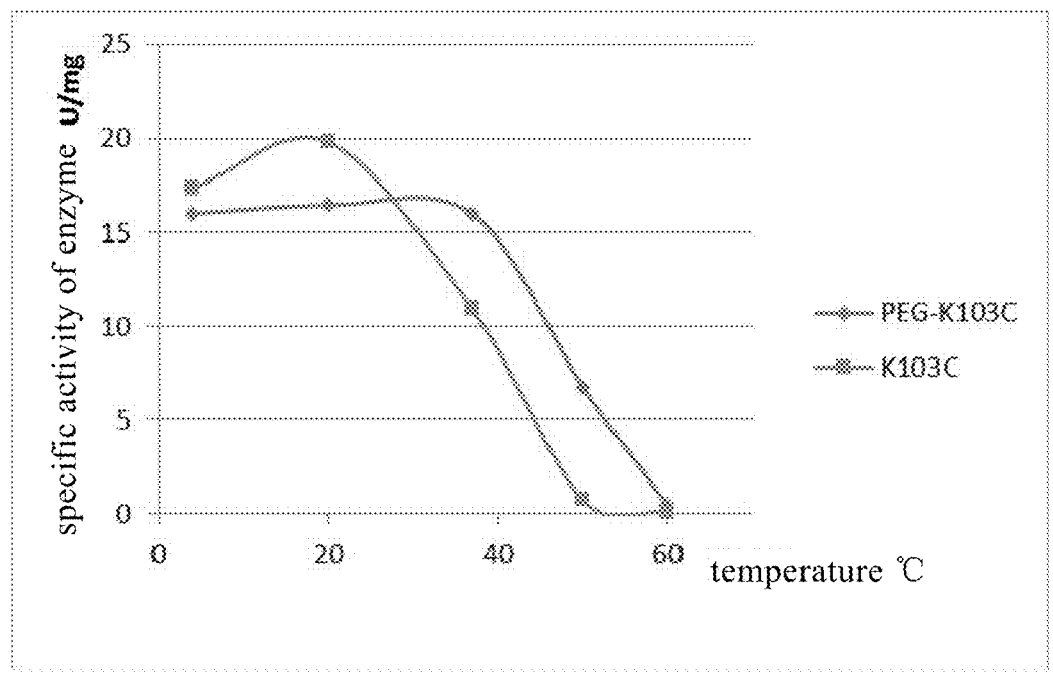
FIG. 7 shows a comparison result of thermal stability between a PEG-modified recombinant uricase PEG-K103C and an unmodified K103C.

The results were shown in FIG. 6 and FIG. 7.

The above results showed that the mutant uricase K103C had a wider range of pH tolerance after PEG modification, especially at physiological pH, the activity was greatly improved, and the thermal stability was also improved. After incubated at 40° C. for 2 hours, the good activity was still maintained.

5.2 Determination of Michaelis Constant

By comparing Michaelis constant, the maximum enzymatic reaction rate and the catalytic constant of the mutant K103C before and after PEG modification, the effect of PEG modification on mutant uricase was evaluated.

TABLE 4

Michaelis constant calculation for PEG-K103C

| [S] (μM) | | absorbance A290 (mAu) | |
|---|---|---|---|
| 0.04 | 25.00 | 0.0269 | 37.24 |
| 0.06 | 16.67 | 0.0283 | 35.29 |
| 0.08 | 12.50 | 0.0302 | 33.07 |
| 0.10 | 10.00 | 0.0309 | 32.40 |
| 0.12 | 8.33 | 0.0310 | 32.29 |

The data below was obtained by software calculation and analysis:
Km=0.0108 ΔAmax=0.034 slope=0.3184 R2=0.9713
Vmax=1.823 μM/min kcat=743.78 min-1

TABLE 5

Michaelis constant calculation for the recombinant urate oxidase K103C

| [S] (μM) | | absorbance A290 (mAu) | |
|---|---|---|---|
| 0.04 | 25.00 | 0.0310 | 32.31 |
| 0.06 | 16.67 | 0.0344 | 29.10 |
| 0.08 | 12.50 | 0.0344 | 29.10 |
| 0.10 | 10.00 | 0.0367 | 27.27 |
| 0.12 | 8.33 | 0.0361 | 27.72 |

The data below was obtained by software calculation and analysis:

Km=0.0114 ΔAmax=0.040 slope=0.2891 R2=0.9265
Vmax=2.333 μM/min kcat=951.84 min-1

The results were shown in Table 4, Table 5. The results showed that after PEG modification, the mutant K103C exhibited little change in Michaelis constant, indicating that the modification of PEG did not shield active sites of the enzyme, largely retaining the affinity of the enzyme to the substrate; however, the maximum reaction rate and catalytic constant after enzyme modification were slightly lower than that before modification, which may be related to the "wrapping" effect of PEG on the enzyme, thereby making the enzymatic reaction more gentle and more suitable for the physiological environment in vivo.

5.3 Determination of the Half-Life 30 5-week-old BABL/C male mice (20 g±2 g), were randomly divided into 3 groups. In Group 1 (10 mice), PEG-modified recombinant uricase PEG-K103C was injected via tail vein at a dose of 10 mg/kg. After 2 h, 4 h, 8 h, 16 h, 24 h, 36 h, 48 h, 72 h, 96 h, 120 h, eyes were removed, the blood was collected and centrifuged, and the supernatant was obtained. The supernatant was then diluted by 20-fold for determining the uricase activity in plasma. In Group 2 (10 mice), recombinant uricase K103C was injected via tail vein at a dose of 10 mg/kg. After 5 min, 15 min, 30 min, 45 min, 1 h, 2 h, 4 h, 8 h, 16 h, 24 h, eyes were removed, the blood was collected and centrifuged, and the supernatant was obtained. The supernatant was then diluted by 20-fold for determining the uricase activity in plasma. In Group 3, 10 mice were used as a control group, and an equal volume of saline was injected. After 5 min, 15 min, 30 min, 45 min, 1 h, 2 h, 4 h, 8 h, 16 h, 24 h, eyes were removed, the blood was collected and centrifuged, and the supernatant was obtained. The supernatant was then diluted by 20-fold for determining the uricase activity in plasma.

Figure 8:
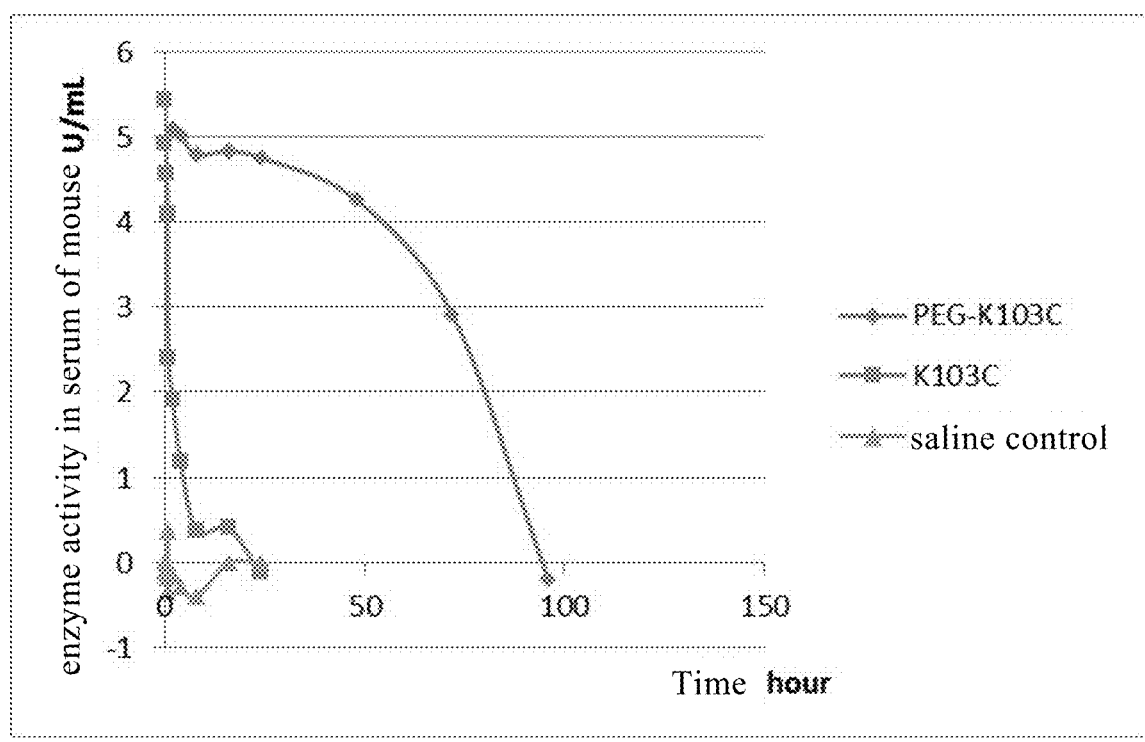
FIG. 8 shows a serum enzyme activity-time profile in mice after a single administration of a PEG-modified recombinant protein PEG-K103C and an unmodified K103C.

The results were shown in FIG. 8. The results showed that the half-life of the mutant uricase K103C in serum was about 1 h, the enzyme activity could only be maintained up to 24 h; whereas PEG-modified enzyme reduced the rate of degradation in mice due to the "wrapping effect" of PEG, the half-life was about 72 h, and the longest action time could reach 96 h.

All literatures mentioned in the present application are incorporated by reference herein, as though individually incorporated by reference. Additionally, it should be understood that after reading the above teaching, many variations and modifications may be made by the skilled in the art, and these equivalents also fall within the scope as defined by the appended claims.

The invention claimed is:

1. A mutant uricase, which has a recombinantly introduced cysteine residue, and the cysteine residue is located in an inactive region of the uricase;
   the inactive region is a region of uricase selected from a group consisting of:
   (a) positions 148±1, 202±1, 228±1, 291±1 of uricase; and
   (b) after the C-terminus of uricase;
   wherein the amino acid position is based on the uricase sequence as shown in SEQ ID NO.: 1, and wherein the introduction of the recombinantly introduced cysteine residue includes substitution, insertion, and/or addition.

2. The mutant uricase of claim 1, wherein the mutant uricase is PEGylated, and the PEGylation site is the position of the recombinantly introduced cysteine residue.

3. A pharmaceutical composition, which comprises:
   the pegylated mutant uricase of claim 2; and
   a pharmaceutically acceptable carrier.

4. The mutant uricase of claim 1, wherein the inactive region is a region of uricase selected from a group consisting of: positions 148, 202, 228, and 291 of uricase.

5. The mutant uricase of claim 1, wherein the recombinantly introduced cysteine residue is introduced by substitution.

6. The mutant uricase of claim 1, wherein the recombinantly introduced cysteine residue is selected from a group consisting of: N148C, G202C, K228C, K291C, and a combination thereof.

7. The mutant uricase of claim 1, wherein the mutant uricase has an average specific activity of ≥10 U/mg.

8. The mutant uricase of claim 1, wherein the mutant uricase has an average specific activity of 12-30 U/mg.

9. The mutant uricase of claim 2, wherein the mutant uricase has an average specific activity of ≥10 U/mg.

* * * * *